(12) United States Patent
Freund et al.

(10) Patent No.: US 7,691,596 B2
(45) Date of Patent: Apr. 6, 2010

(54) METHODS FOR DETERMINING GTP CYCLOHYDROLASE I OR II ACTIVITY

(75) Inventors: Annette Freund, Limburgerhof (DE); Franz Röhl, Schifferstadt (DE); Henning Althöfer, Wachenheim (DE); Marvin Karos, Neustadt (DE); Bruno Kaesler, Ludwigshafen (DE); Thierry Lacour, Stutensee (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/205,441

(22) Filed: Sep. 5, 2008

(65) Prior Publication Data

US 2009/0023172 A1 Jan. 22, 2009

Related U.S. Application Data

(62) Division of application No. 11/477,874, filed on Jun. 29, 2006, now Pat. No. 7,435,557, which is a division of application No. 10/526,207, filed as application No. PCT/EP03/09369 on Aug. 23, 2003, now abandoned.

(30) Foreign Application Priority Data

Sep. 6, 2002 (EP) .................... 02020051

(51) Int. Cl.
*C12Q 1/34* (2006.01)
(52) U.S. Cl. ........................................ 435/18
(58) Field of Classification Search ............... 435/18
See application file for complete search history.

(56) References Cited

U.S. PATENT DOCUMENTS 5,821,090 A 10/1998 Revuelta Doval et al.

6,171,598 B1 1/2001 Wang et al.

FOREIGN PATENT DOCUMENTS

| JP | 60 030696 A | 2/1985 |
| SU | 1271873 | 10/1984 |
| WO | WO-00/22133 | 4/2000 |
| WO | WO-00/40744 | 7/2000 |

OTHER PUBLICATIONS

XP002233356, "Database WPI", Section Ch, Week 198513, Derwent Publications Ltd., London, GB; , An 1985-078062.
Blau, N., et al.,"The Application of 8 Amino-GTP a New Inhibitor of GTP Cyclohydrolase I to the Purification of the Enzyme from Human Liver", Biochimica Et Biophysica ACTA, vol. 880, No. 1, 1986, pp. 26-31.
Forr, et al., "GTP Cyclohydrolase II from *Escherichia coli*", Methods in Enzymology, vol. 66, 1980, pp. 303-307.
Maier, J. ,et al., "Homology Cloning of GTP-cyclohydrolase I from Fungi and Plants by Reverse-Transcription PCT Using a General Set of Degenerate Primers", Pteridines 1995 Germany, vol. 6, No. 3, 1995, pp. 112-115.
Ritz, Harald ,et al., "Biosynthesis of Riboflavin: Studies on the Mechanism of GTP Cyclohydrolase II", Journal of Biological Chemistry, vol. 276, No. 25, Jun. 22, 2001, pp. 22273-22277.
Saccharomyces Genome Database (SGD); http://db.yeastgenome.org, multiple pages, printed on Dec. 16, 2004.
Swiss-Prot Protein Sequence Database, Accession No. P 47924, printed on Dec. 16, 2004.
Swiss-Prot Protein Sequence Database, Accession No. P 25523, printed on Dec. 16, 2004.

*Primary Examiner*—Ralph Gitomer
(74) *Attorney, Agent, or Firm*—Brinks Hofer Gilson & Lione (57) ABSTRACT

The present invention relates to methods for determining GTP Cyclohydrolase I or II activity in a sample.

3 Claims, 1 Drawing Sheet

METHODS FOR DETERMINING GTP CYCLOHYDROLASE I OR II ACTIVITY

This application is a divisional of application Ser. No. 11/477,874, filed on Jun. 29, 2006, now U.S. Pat. No. 7,435,557, which is a divisional of application Ser. No. 10/526,207, filed Mar. 4, 2005, now abandoned, which is the National Stage of International Application No. PCT/EP2003/009369, filed Aug. 23, 2003, and which claims priority to European Patent Application No. 02020051.5, filed on Sep. 6, 2002. The entire contents of these applications are hereby incorporated by reference herein.

DETAILED DESCRIPTION

The present invention relates to the identification of fungal GTP cyclohydrolase II as a target for fungicides, to a method for identifying antifungal agents based on fungal GTP cyclohydrolase II, and also to the use of compounds identified as fungicides via the abovementioned method.

The basic principle of identifying fungicides via inhibition of a defined enzyme is known (WO 00/3657). With regard to the increasing problems regarding resistance to fungicides, however, there exists a great need for detecting enzymes which might constitute novel targets for fungicides.

In practice, the detection of targets is extremely difficult, since often the inhibition of an enzyme participating in a biochemical pathway does not lead to decreased growth or infectivity of the pathogenic fungi. A putative reason is the existence of an alternative, may be unknown pathway used by the fungus. Thus, even if the function of the gene itself is known, it is not possible to predict a fitness for use as a fungicide target.

Thus, it is an object of the present invention to identify a novel fungicide target.

Surprisingly, we have found that fungal GTP cyclohydrolase is suitable as a fungicide target. The present invention comprises the use of a fungal GTP cyclohydrolase as target for the identification of antifungal agents and methods of identifying antifungal agents which inhibit fungal GTP cyclohydrolase II comprising the following steps:

i. incubating, with at least one candidate compound, a fungal GTP cyclohydrolase II under conditions allowing the binding of the candidate compound to the fungal GTP cyclohydrolase II polypeptide; and ii. selecting, by step ii), at least one candidate compound which binds to the fungal GTP cyclohydrolase II of step i); or iii. selecting, by step iii), at least one candidate compound which reduces or blocks the activity of the fungal GTP cyclohydrolase II of step i); or iv. selecting, by step iv), at least a candidate compound which inhibits or decreases transcription, translation or expression of the fungal GTP cyclohydrolase II of step i).

Some of the terms used in the description are defined at this point.

"Affinity tag": this denotes a peptide or polypeptide whose coding nucleic acid sequence can be fused to the sequence encoding the fungal GTP cyclohydrolase II, either directly or using a linker, by customary cloning techniques. The affinity tag serves to isolate the recombinant fungal GTP cyclohydrolase II by means of affinity chromatography. The abovementioned linker can optionally comprise a protease cleavage site (for example for thrombin or factor Xa), whereby the affinity tag can be cleaved off from the fungal GTP cyclohydrolase II, as required. Examples of customary affinity tags are the "his-tag", for example from Quiagen, Hilden, "strep-tag", "myc-tag" (Invitrogen, Carlsberg), New England Biolab's tag which consists of a chitin-binding domain and an intein, and what is known as the CBD-tag from Novagen.

"Antifungal agents" are agents against pathogenic fungi such as human and plant pathogens, preferably plant pathogens.

"Enzymatic activity/activity assay": the term enzymatic activity describes the ability of an enzyme to convert a substrate into a product. In this context, both the natural substrate of the enzyme and a synthetic modified analog of the natural substrate can be used. The enzymatic activity can be determined in what is known as an activity assay via the increase in the product, the decrease in the starting material, the decrease or increase in a specific cofactor, or a combination of at least two of the aforementioned parameters as a function of a defined period of time. If the enzyme catalyzes a reversible reaction, both the starting material and the product may be employed as substrate in the activity assay in question.

"Expression cassette or nucleic acid sequence": an expression cassette comprising a nucleic acid sequence according to the invention operatively linked to a promotor and/or terminator sequence is understood as meaning, for example, a genomic or a complementary DNA sequence or an RNA sequence and semisynthetic or fully synthetic analogs of these. These sequences may be present in linear or circular form, extrachromosomally or integrated into the genome. The nucleic acid sequences according to the invention can be generated synthetically or obtained naturally or comprise a mixture of synthetic and natural DNA components, and be composed of a variety of heterologous gene segments of various organisms.

Artificial nucleic acid sequences too are suitable in this context as long as they make possible the expression of the fungal GTP cyclohydrolase II in a cell or an organism. For example, synthetic nucleotide sequences can be generated which were optimized with regard to the codon usage of the organisms to be transformed.

All of the abovementioned nucleotide sequences can be generated in a manner known per se by chemical synthesis from the nucleotide units such as, for example, by fragment condensation of individual overlapping complementary nucleotide units of the double helix. Oligonucleotides can be synthesized chemically for example in a known manner using the phosphoamidite method (Voet, Voet, 2nd Edition, Wiley Press New York, pages 896-897). When preparing an expression cassette, a variety of DNA fragments can be manipulated to give rise to a nucleotide sequence which reads in the correct direction and is in-frame. The nucleic acid fragments are linked to each other by general cloning techniques as are described, for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1994).

"Gene" describes a nucleic acid sequence which encodes a protein and which can be transcribed into RNA (mRNA, rRNA, tRNA, snRNA, sense RNA or antisense RNA) and which can optionally be associated with regulatory sequences. Examples of regulatory sequences are promoter sequences. Other elements which are optionally present are, for example, introns.

"Genetic control sequence": the term of the genetic control sequences (which is equivalent to the term "regulatory sequence") describes sequences which have an effect on the materialization or the function of the expression cassette according to the invention and which ensure for example transcription and, if appropriate, translation in prokaryotic or eukaryotic organisms. Examples are promoters or what are known as enhancer sequences. In addition to these control sequences, or instead of these sequences, the natural regulation of these sequences before the actual structural genes may still be present and, if appropriate, may have been modified genetically in such a way that the natural regulation has been inactivated and the expression of the fungal GTP cyclohydrolase II gene increased. The choice of the control sequence depends on the host organism or starting organism. Genetic control sequences furthermore also encompass the 5'-untranslated region, introns or the noncoding 3'-region of genes. Control sequences are furthermore understood as being those which make possible a homologous recombination or insertion into the genome of a host organism or which permit the removal from the genome.

"Functional equivalents" in the present context describe nucleic acid sequences which hybridize under standard conditions with the nucleic acid sequence encoding the GTP cyclohydrolase II or portions of the nucleic acid sequence encoding the GTP cyclohydrolase II, and which are capable of bringing about the expression of an enzymatically active fungal GTP cyclohydrolase II in a cell or an organism.

It is advantageous to use short oligonucleotides of a length between 10 to 50 bp, preferably 15-40 bp, for example of the conserved or other regions, which can be determined via comparisons with other related genes in a manner known to the skilled worker for the hybridization. Alternatively, it is also possible to use longer fragments of the nucleic acids according to the invention or the complete sequences for the hybridization. These standard conditions vary depending on the nucleic acid used, viz. oligonucleotide, longer fragment or complete sequence, or depending on which type of nucleic acid, viz. DNA or RNA, is being used for the hybridization. Thus, for example, the melting temperatures for DNA:DNA hybrids are approx. 10° C. lower than those of DNA:RNA hybrids of equal length.

Standard conditions are understood as meaning, depending on the nucleic acid, for example temperatures between 42 and 58° C. in an aqueous buffer solution with a concentration of between 0.1 and 5×SSC (1×SSC=0.15 M NaCl, 15 mM sodium citrate, pH 7.2) or additionally in the presence of 50% formamide such as, for example, 42° C. in 5×SSC, 50% formamide. The hybridization conditions for DNA:DNA hybrids are advantageously 0.1×SSC and temperatures of between approximately 20° C. and 45° C., preferably between approximately 30° C. and 45° C. The hybridization conditions for DNA:RNA hybrids are advantageously 0.1× SSC and temperatures of between approximately 30° C. and 55° C., preferably between approximately 45° C. and 55° C. These temperatures stated for the hybridization are melting temperature values which have been calculated by way of example for a nucleic acid with a length of approx. 100 nucleotides and a G+C content of 50% in the absence of formamide. The experimental conditions for DNA hybridization are described in specialist textbooks of genetics such as, for example, Sambrook et al., "Molecular Cloning", Cold Spring Harbor Laboratory, 1989 and can be calculated using formulae known to the skilled worker, for example as a function of the length of the nucleic acids, the type of the hybrids or the G+C content. The skilled worker can find more information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

A functional equivalent is furthermore also understood as meaning, in particular, natural or artificial mutations of the relevant nucleic acid sequences of the fungal GTP cyclohydrolase II and their homologs from other organisms which make possible the expression of the enzymatically active fungal GTP cyclohydrolase II in a cell or an organism.

Thus, the scope of the present invention also extends to, for example, those nucleotide sequences which are obtained by modification of the nucleic acid sequence of a GTP cyclohydrolase II. The purpose of such a modification can be, for example, the insertion of further cleavage sites for restriction enzymes, the removal of excess DNA, or the addition of further sequences. Proteins which are encoded via said nucleic acid sequences should still maintain the desired functions, despite the deviating nucleic acid sequence.

The term functional equivalent may also refer to the protein encoded by the nucleic acid sequence in question. In this case, the term functional equivalent describes a protein whose amino acid sequence is up to a specific percentage homologous to or identical with that of the GTP cyclohydrolase II.

Functional equivalents thus encompass naturally occurring variants of the sequences described herein, and also artificial, for example chemically synthesized, nucleic acid sequences adapted to the codon usage, or the amino acid sequences derived therefrom.

In general, it can be said that functional equivalents independently of the amino acid sequence in question (encoded by a corresponding nucleic acid sequence) have in each case the enzymatic activity of a GTP cyclohydrolase II.

"GTP cyclohydrolase II activity" denotes the ability of an enzyme to catalyse a reaction, wherein GTP is metabolized into 2,5-diamino-6-ribosylamino-4(H)-pyrimidinone 5'-monophosphate, pyrophosphoric acid and formic acid.

"Homology" between two nucleic acid sequences or polypeptide sequences is defined by the identity of the nucleic acid sequence/polypeptide sequence by in each case the entire sequence length, which is calculated by alignment with the aid of the program algorithm GAP (Wisconsin Package Version 10.0, University of Wisconsin, Genetics Computer Group (GCG), Madison, USA), setting the following parameters:

| | |
|---|---|
| Gap weight: 8 | Length weight: 2 |
| Average match: 2,912 | Average mismatch: −2,003 |
| matrix BLOSUM 62 | |

The term "homology" is used herein as a synonym for "identity".

"Mutations" comprise substitutions, additions, deletions, inversions or insertions of one or more nucleotide residues, which may also lead to a modification of the corresponding amino acid sequence of the fungal GTP cyclohydrolase II by substitution, insertion or deletion of one or more amino acids.

"Knock-out transformant" refers to a transgenic organism, in which a specific gene has been inactivated in a directed fashion by means of transformation.

"Natural genetic environment" is understood as meaning the natural chromosomal locus in the organism of origin or the presence in a genomic library. In the case of a genomic library, the natural genetic environment of the nucleic acid sequence is preferably retained at least in part. The environment flanks the nucleic acid sequence at least on the 5' or 3' side and has a sequence length of at least 50 bp, preferably at least 100 bp, especially preferably at least 500 bp, very especially preferably at least 1000 bp, most preferably at least 5000 bp.

"Operative linkage": An operative or else functional linkage is understood as meaning the sequential arrangement of promoter, coding sequence, terminator and, if appropriate, further regulatory elements in such a way that each of the regulatory elements can, upon expression of the coding sequence, fulfil its function as intended.

"Recombinant DNA" describes a combination of DNA sequences in an arrangement other than their natural arrangement, which can be generated by recombinant DNA technology, but also DNA comprising the endogenous and foreign or synthetic DNA, also homologous and heterologous DNA based on the relatedness of the organisms.

"Recombinant DNA technology": generally known techniques from fusing DNA sequences (for example described in Sambrook et al., 1989, Cold Spring Harbor, N.Y., Cold Spring Harbor Laboratory Press).

"Origins of replication" ensure the amplification of the expression cassettes or vectors according to the invention in microorganisms, for example pBR322 ori or P15A ori in *E. coli* (Sambrook et al.: Molecular Cloning. A Laboratory Manual, 2nd ed. Cold Spring Harbor Laboratory Press, Cold Spring Harbor, N.Y., 1989).

"Reporter genes" encode readily quantifiable proteins. Using these genes, an assessment of transformation efficacy or of the site or time of expression can be made via growth, fluorescence, chemoluminescence, bioluminescence or resistance assay or via photometric measurement (intrinsic color) or enzyme activity. Very especially preferred in this context are reporter proteins (Schenborn E, Groskreutz D. Mol. Biotechnol. 1999; 13(1):29-44) such as the "green fluorescence protein" (GFP) (Gerdes H H and Kaether C, FEBS Lett. 1996; 389(1):44-47; Chui W L et al: Curr. Biol. 1996, 6:325-330; Leffel S M et al., Biotechniques. 23(5):912-8, 1997), chloramphenicol acetyl transferase, a luciferase (Giacomin, Plant Sci. 1996, 1.16:59-72; Scikantha, J. Bact. 1996, 178: 121; Millar et al., Plant Mol. Biol. Rep. 1992 10:324-414), and luciferase genes, in general β-galactosidase or β-glucuronidase (Jefferson et al., EMBO J. 1987, 6, 3901-3907), the Ura3 gene, the Ilv2 gene, the 2-desoxyglucose-6-phosphate phosphatase gene, β-lactamase gene, the neomycin phosphotransferase gene, the hygromycin phosphotransferase gene, or the BASTA (=gluphosinate) resistance gene.

"Selection markers" impart resistance to antibiotics. Examples which may be mentioned are the neomycin-phosphotransferase-gen gene, which imparts resistance to the aminoglyciside antibiotics neomycin (G 418), kanamycin and paromycin (Deshayes A et al., EMBO J. 4 (1985) 2731-2737), the sul gene (Guerineau F et al., Plant Mol. Biol. 1990; 15(1):127-136), the hygromycin B phosphotransferase-Gen (Gen Bank Accession NO: K 01193) and the she-ble gene, which imparts resistance to the bleomycin antibiotic zeocin. Other examples of selection marker genes are genes which impart resistance to 2-desoxyglucose-6-phosphate (WO 98/45456) or phosphinothricin and the like, or those which impart resistance to antimetabolites, for example the dhfr gene (Reiss, Plant Physiol. (Life Sci. Adv.) 13 (1994) 142-149). Also suitable are genes such as trpB or hisD (Hartman S C and Mulligan R C, Proc. Natl. Acad. Sci. USA. 85 (1988) 8047-8051). Also suitable are the mannose-phosphate isomerase gene (WO 94/20627), the ODC (ornithin decarboxylase) gene (McConlogue, 1987 in: Current Communications in Molecular Biology, Cold Spring Harbor Laboratory, Ed.), or the *Aspergillus terreus* deaminase (Tamura K et al., Biosci. Biotechnol. Biochem. 59 (1995) 2336-2338).

"Significant decrease": referring to the enzymatic activity, is understood as meaning the decrease in the enzymatic activity of the enzyme incubated with a candidate compound in comparison with the activity of an enzyme not incubated with the candidate compound, which lies outside an error in measurement.

"Substrate": Substrate is the compound which is recognized by the enzyme in its original function and which is converted into a product by means of a reaction catalyzed by the enzyme.

"Transgenic": Referring to a nucleic acid sequence, an expression cassette or a vector comprising said nucleic acid sequence or an organism transformed with said nucleic acid sequence, expression cassette or vector, transgenic describes all those constructions generated by recombinant methods in which either the nucleic acid sequence of the fungal GTP cyclohydrolase II or a genetic control sequence linked operably to the nucleic acid sequence of the fungal GTP cyclohydrolase II or a combination of both of the aforementioned nucleic acid sequences.

GTP cyclohydrolase II catalyses the first step in the biosynthesis of riboflavin (vitamin B2), wherein GTP is metabolized into 2,5-diamino-6-ribosylamino-4(H)-pyrimidinone 5'-monophosphate, pyrophosphoric acid and formic acid (Ritz et. al. JBC 2001, 276: 22273-22277). GTP cyclohydrolase II can be used for fermetative riboflavin synthesis in *Ashbya gossypii* (WO 95/26406).

In plants, GTP cyclohydrolase II is used as a target for herbicides (WO 00/40744). The plant enzyme, however, differs significantly from the fungal enzyme. The identity between fungal GTP cyclohydrolase II from *Ashbya gossypii* (SEQ ID NO:2) and plant GTP cyclohydrolase II from *Arabidopsis thaliana* (SWISS-PROT P47924) is only 31%. The identity between bacterial GTP cyclohydrolase II from *Escherichia coli* (SWISS-PROT P25523) and SEQ ID NO:2 is 48%.

Experiments in the yeast *Saccharomyces cerevisiae* indicate that GTP cyclohydrolase II is not essential for yeast (*Saccharomyces* Genom Database (SGD); http://genome-www.stanford.edu/Saccharomyces/ see for http://genome-www4.stanford.edu/cgi-bin/SGD/phenotype/phenotype.pl?feat=RIB1&type=locus.

Surprisingly, it was found that GTP cyclohydrolase II is a suitable fungicide target by demonstrating the essential role of GTP cyclohydrolase II for the pathogenic filamentous fungi *Ashbya gossypii*. The present invention therefore provides methods of using a fungal GTP cyclohydrolase II polypeptide (used herein synonymous to fungal GTP cyclohydrolase II) encoding nucleic acid sequence to identify inhibitors thereof, which then can be used as fungicides to suppress the growth of pathogenic fungi.

The term "pathogenic fungi" denotes fungi which colonize a host (a plant or a mammal) and cause disease, e.g. human pathogenens selected from the group consisting of the genera and species *Candida* such as *Candida albicans, Candida stettatoidea, Candida tropicatis, Candida parapsilosis, Candida krusei, Candida pseudotropicatis, Candida quittermondii, Candida rugosa, Aspergillus* such as *Aspergillus fumigatus, Aspergillus flavus, Aspergillus niger, Aspergillus nidulans, Aspergillus terreus, Rhizopus* such as *Rhizopus arrhizus, Rhizopus oryzae, Absidia* such as *Absidia corymbifera, Absidia ramosa* and *Mucor* such as *Mucor pusiltus* or phytopathogenic filamentous fungi selected from the group consisting of the genera and species *Ashbya* such as *Ashbya gossypii, Alternaria, Podosphaera, Sclerotinia, Physalospora* such as *Physalospora canker, Botrytis* species such as *Botrytis cinerea, Corynespora* such as *Corynespora melonis; Colletotrichum; Diplocarpon* such as *Diplocarpon rosae; Elsinoe* such as *Elsinoe fawcetti, Diaporthe* such as *Diaporthe citri; Sphaerotheca; Cinula* such as *Cinula neccata, Cercospora; Erysiphe* such as *Erysiphe cichoracearum* and *Erysiphe graminis; Sphaerotheca* such as *Sphaerotheca fuliginea; Leveillula* such as *Leveillula taurica; Magnaporte* species such as *Magnaporthe (M.) grisea, Mycosphaerella; Phyllactinia* such as *Phyllactinia kakicola; Gloesporium* such as *Gloesporium kaki; Gymnosporangium* such as *Gymnosporangium yamadae, Leptotthrydium* such as *Leptotthrydium pomi, Podosphaera* such as *Podosphaera leucotricha; Pyrenophora (P.)* such as *P. graminea, P. hordei, P. japonica, P. teres, P. teres* f. *maculata, P. teres* f. *teres, P. tritici-repentis, Gloedes* such as *Gloedes pomigena; Cladosporium* such as *Cladosporium carpophilum; Phomopsis; Phytopora; Phytophthora* such as *Phytophthora infestans; Verticillium; Glomerella* such as *Glomerella cingulata; Drechslera; Bipolaris; Personospora; Phaeoisariopsis* such as *Phaeoisariopsis vitis; Spaceloma* such as *Spaceloma ampelina; Pseudocercosporella* such as *Pseudocercosporella herpotrichoides; Pseudoperonospora; Puccinia; Typhula; Pyricularia* such as *Pyricularia oryzae; Rhizoctonia; Stachosporium* such as *Stachosporium nodorum; Uncinula* such as *Uncinula necator; Ustilago* such as *Ustilago maydis; Gaeumannomyces* species such as *Gaeumannomyces graminis* and *Fusarium (F.)* such as *F. dimerium, F. merismoides, F. lateritium, F. decemcellulare, F. poae, F. tricinctum, F. sporotrichioides, F. chlamydosporum, F. moniliforme, F. proliferatum, F. anthophilum, F. subglutinans, F. nygamai, F. oxysporum, F. solani, F. culmorum, F. sambucinum, F. crookwellense, F. avenaceum* ssp. *avenaceum, F. avenaceum* ssp. *aywerte, F. avenaceum* ssp. *nurragi, F. hetrosporum, F. acuminatum* ssp. *acuminatum, F. acuminatum* ssp. *armeniacum, F. longipes, F. compactum, F. equiseti, F. scripi, F. polyphialidicum, F. semitectum* and *F. beomiforme*, preferably, the term "pathogenic fungi" denotes filamentous phytopathogenic fungi mentioned above.

In one embodiment, the present invention encompasses a method for identifying antifungal agents comprising the following steps:

i. incubating, with at least one candidate compound, a fungal GTP cyclohydrolase II under conditions allowing the binding of the candidate compound to the fungal GTP cyclohydrolase II; and ii. selecting, by step ii), at least one candidate compound which binds to the fungal GTP cyclohydrolase II of step i); or iii. selecting, by step iii), at least one candidate compound which reduces or blocks the activity of the fungal GTP cyclohydrolase II of step i); or iv. selecting, by step iv), at least a candidate compound which inhibits or decreases transcription, translation or expression of the fungal GTP cyclohydrolase II.

Preferably, the fungal GTP cyclohydrolase II is encoded by a nucleic acid sequence comprising a) a nucleic acid sequence shown in SEQ ID NO:1; or b) a nucleic acid sequence which, owing to the degeneracy of the genetic code, can be deduced from the amino acid sequence shown in SEQ ID NO: 2 by back translation; or c) a nucleic acid sequence which, owing to the degeneracy of the genetic code, can be deduced from a functional equivalent of the amino acid sequence shown in SEQ ID NO: 2, which has an identity with SEQ ID NO:2 of at least 49%, by back translation.

The functional equivalent of SEQ ID NO:2 set forth in c) has an identity of at least 49%, 50%, 51%, 52%, 53%, 54%, 55%, 56%, 57% preferably at least 58%, 59%, 60%, 61%, 62%, 63%, 64%, 65%, 66%, 67%, 68%, 69%, and 70% more preferably 71%, 72%, 73%, 74%, 75%, 76%, 77%, 78%, 79%, 80%, 81%, 82%, 83%, 84%, 85% most preferably at least 86%, 87%, 88%, 89%, 90%, 91%, 92%, 93%, 94%, 95%, 96%, 97%, 0.98%, 99% homology with the SEQ ID NO:2.

The nucleic acid sequence originates from a fungus, wherein the term fungus denotes the above-mentioned pathogenic fungi and yeast such as *Saccharomyces* species (e.g. *S. cerevisiae*), *Pichia* species (e.g. *P. pastoris, P. methanolica*), *Schizosaccharomyces* species (e.g. *Schizosaccharomyces pombe*) and *Klyveromyces* species (e.g. *K. lactis*).

Within the scope of the present invention also novel nucleic acid sequences encoding a fungal GTP cyclohydrolase are provided, whereby said nucleic acid sequences comprise a) a nucleic acid sequence shown in SEQ ID NO:4; or b) a nucleic acid sequence which, owing to the degeneracy of the genetic code, can be deduced from the amino acid sequence shown in SEQ ID NO:5 by back translation; or c) a nucleic acid sequence which, owing to the degeneracy of the genetic code, can be deduced from a functional equivalent of the amino acid sequence shown in SEQ ID NO:5, which has an identity with SEQ ID NO:5 of at least 66%, by back translation.

The functional equivalent of SEQ ID NO:4 set forth in c) has an identity of at least 66%, 67%, 68%, 69%, 70%, 71%, 72%, 73%, 74%, 75%, 76%, preferably at least 77%, 78%, 79%, 80%, 81%, 82%, 83%, more preferably 84%, 85%, 86%, 87%, 88%, 89%, 90%, 91% most preferably at least 92%, 93%, 94%, 95%, 96%, 97%, 98%, 99% homology with the SEQ ID NO:5.

The selection according to step ii) can be based on binding assays detecting the protein-inhibitor interactions, wherein either the candidate compound or fungal GTP cyclohydrolase II comprises a detectable label, such as a fluorescent, radioisotopic, chemiluminescent, or enzymatic label, such as horseradish peroxidase, alkaline phosphatase, or luciferase. Detection of a candidate compound, which is bound to the fungal GTP cyclohydrolase II can then be accomplished, for example, by direct counting of radio-emmission, by scintillation counting, or by determining conversion of an appropriate substrate to a detectable product.

Preferred examples of these binding assays are fluorescence correlation spectroscopy (FCS) (Proc. Natl. Acad. Sci. USA (1994) 11753-11575), flurescence polarization (Methods in Enzymology 246 (1995), pp. 283-300) or Fluorescence Energy Transfer (FRET) (Cytometry 34, 1998, pp. 159-179; homogeneous Time Resolved Fluorescence (HTRF) is preferred, if FRET is to be used).

Alternatively, binding of a candidate compound to a fungal GTP cyclohydrolase II can be determined without labeling either of the interactants, e.g. by using a microphysiometer to detect binding of a candidate compound to the fungal GTP cyclohydrolase II. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a candidate compound and fungal GTP cyclohydrolase II (according to McConnell et al., Science 2.57, 19061912, 1992). In addition, determining the ability of a candidate compound to bind to the fungal GTP cyclohydrolase II can be accomplished using a technology such as real-time Bimolecular Interaction Analysis (BIA) (Sjolander & Urbaniczky, Anal. Chem. 63, 23382345, 1991, and Szabo et al., Curr. Opin. Struct. Biol. 5,699705, 1995), a technology for studying biospecific interactions in real time, without labeling any of the interactants (e.g. BIAcore). Changes in the optical phenomenon surface plasmone resonance can be used as an indication of real-time reactions between biological molecules. Also surface-enhanced laser desorption/ionization (SELDI) in combination with a time-off-light mass spectrometer (MALDI-TOF) makes the rapid analysis of molecules on a support possible and can be used for analyzing protein-ligand interactions (Worral et al., (1998) Anal. Biochem. 70:750-756).

Alternatively, all of the above-mentioned methods can be based on a "competition assay", wherein a reference molecule is replaced by the candidate compound.

It is also possible to detect further potential antifungal agents by "molecular modeling" via elucidation of the three-dimensional structure of the polypeptide according to the invention using x-ray structure analysis. The preparation of protein crystals required for x-ray structure analysis, and the corresponding measurements and subsequent evaluations of said measurements, as well as the methodology of "molecular modeling" are known to the skilled worker. In principle, optimization via "molecular modeling" of the active ingredients identified by the above-mentioned methods is also possible.

The selection according to steps iii) and iv) preferably comprises testing a candidate compound in a fungal GTP cyclohydrolase II inhibition assay.

By preference, the selection according to step iii), hereinafter referred to as "in vitro assay", is based on the following steps:
a) incubating, with a candidate compound, the fungal GTP cyclohydrolase II in a cell free system;
b) selecting, by step b), a candidate compound which decreases the activity of fungal GTP cyclohydrolase II.

The enzymatic activity of the fungal GTP cyclohydrolase II is preferably determined in comparison to the activity of a fungal GTP cyclohydrolase II not incubated with the candidate compound.

In step (b), candidate compounds are selected which brought about a significant decrease in the enzymatic activity corresponding to a reduction of at least 10%, advantageously at least 20%, preferably at least 30%, especially preferably by at least 50% and very especially preferably by at least 70%, or a 100% reduction (blocking) being achieved.

Suitable substrates added to the reaction mixture in step b) for determination of enzymatic activity are GTP or GTP comprising a detectable label, such as a fluorescent, radioisotopic or chemiluminescent label. These labeled derivatives are hereinafter referred to as "GTP-analogs".

For determination of enzymatic activity of fungal GTP cyclohydrolase II in step b) of the in vitro assay, a fungal GTP cyclohydrolase II comprising mixture (e.g. crude cell extract, partially or totally purified protein) is incubated with a suitable substrate and the conversion of the substrate or the increase in the resultant product is monitored e.g. by HPLC or by measurement of fluorescence, radioactivity or chemiluminescence of the respective sample.

For example, the enzymatic activity can be determined by HPLC as described in Ritz et. al. Journal of Biological Chemistry 2001, 276: 22273-22277) or by monitoring radioactivity as described by Foor and Brown (1980, Meth. Enzymol. 66:303-307). For these methods, GTP cyclohydrolase II is preferably partially purified or purified to homogeneity.

Although there are enzymatic activity assays by which GTP cyclohydrolase II activity can be determined, there is a constant need for development of new methods for determining enzymatic activity that are easy to perform and also suitable for high throughput Screening (HTS).

Surprisingly, it has been found that GTP cyclohydrolase II activity can be successfully determined in the presence of the enzyme formate dehydrogenase (E.C. 1.2.1.2). In this method, the formic acid formed by GTP cyclohydrolase can be linked to the reduction of NAD by the combination of both of these enzymes. The level of formate can be determined by monitoring the formation of NADH preferably by spectroscopy as described by Tishkov and Egorov (SU 1271873).

This method is not only suitable for fungal GTP cyclohydrolase II, but also for plant GTP cyclohydrolase II and GTP cyclohydrolase I [E.C. 3.5.4.16], an enzyme having the same substrate specificity as GTP cyclohydrolase I but a different physiological function: GTP cyclohydrolase I that catalyses the first step in the biosynthesis of tetrahydrofolate and tetrahydrobiopterin. Within the scope of the present invention, this method is used preferably for fungal GTP cyclohydrolase II.

Thus, the present invention encompasses a method for determination of GTP cyclohydrolase activity comprising the following steps:
a) adding GTP or GTP analog, NAD+ and formate dehydrogenase to a sample comprising a GTP cyclohydrolase II or I; and
b) determination of the NADH content.

If the method is used for an inhibition assay, it can comprise the following steps to ensure that the candidate compound inhibits GTP cyclohydrolase II and not formate dehydrogenase:
a) adding GTP or GTP analog, NAD+ and formate dehydrogenase to a sample comprising GTP cyclohydrolase I or II;
b) adding formate, NAD+ and formate dehydrogenase to a second sample comprising fungal GTP cyclohydrolase II;
c) adding to the sample of step a) and step b) a candidate compound;
d) determining the activity of both samples;
e) selecting candidate compounds that show inhibition in the presence of GTP and no inhibition in the presence of formic acid.

Thus, in a particularly preferred embodiment, the GTP cyclohydrolase II activity in step c) of the in vitro assay is determined in the presence of the enzyme formate dehydrogenase (E.C. 1.2.1.2) comprising the following steps:
a) adding GTP or GTP analog, NAD+ and formate dehydrogenase to a sample comprising fungal GTP cyclohydrolase II; and
b) determination of the NADH content.

In another particularly preferred embodiment, the in vitro assay comprises the following steps:
a) adding GTP or GTP analog, NAD+ and formate dehydrogenase to a sample comprising fungal GTP cyclohydrolase II;
b) adding formate, NAD+ and formate dehydrogenase to a second sample comprising fungal GTP cyclohydrolase II;
c) adding to the sample of step a) and step b) a candidate compound;
d) determining the activity of both samples;
e) selecting candidate compounds that show inhibition in the presence of GTP and no inhibition in the presence of formic acid.

This method is suitable even if unpurified cell extracts (lysates) are put in the respective assay. Furthermore, this method is applicable to high throughput screening for inhibitors of fungal GTP cyclohydrolase II. If lysates or enzyme samples are used in which both enzymes, GTP cyclohydrolase I and GTP cyclohydrolase II are present, the selected candidate compounds can be optionally further tested in another inhibition assay to confirm whether GTP cyclohydrolase I or GTP cyclohydrolase II is inhibited (e.g. according to Ritz et. al. Journal of Biological Chemistry 2001, 276: 22273-22277).

The fungal GTP cyclohydrolase II used for the in vitro test can be present in the lysate of the fungi or of the transgenic organism according to the invention. If required, the polypeptide according to the invention can be purified partially or fully by customary methods. A general overview of customary techniques for purification of proteins is given, for example, in Ausubel, F. M. et al., Current Protocols in Molecular Biology, Greene Publishing Assoc. and Wiley-Interscience (1994); ISBN 0-87969-309-6. In the case of recombinant production, purification of the protein fused to an affinity tag may be effected by affinity chromatography.

The fungal GTP cyclohydrolase II used for the above-mentioned in vitro assay can either be expressed in a transgenic organism transformed with an expression cassette comprising a nucleic acid sequence encoding a fungal GTP cyclohydrolase II in enzymatically active form or be obtained by culturing fungi naturally comprising a GTP cyclohydrolase II.

How to perform heterologous expression of an enzyme-like fungal GTP cyclohydrolase II is well known to the skilled artisan. First, appropriate expression cassettes and/or vectors comprising the expression cassette have to be prepared, or alternatively, commercial available vectors can be used. Besides plasmids, vectors are also understood as meaning all the other vectors known to the skilled worker such as, for example, phages, viruses such as SV40, CMV, baculovirus, adenovirus, transposons, IS elements, phasmids, phagemids, cosmids, linear DNA or circular DNA. These vectors are capable of being replicated autonomously in the host organism or replicated chromosomally, chromosomal replication being preferred.

Suitable expression cassette comprises fungal GTP cyclohydrolase II encoding nucleic acid sequence operatively linked to control elements, which govern the expression of the coding sequence in the host cell. In accordance with a preferred embodiment, an expression cassette according to the invention comprises, at the 5' end of the coding sequence, a promoter and at the 3' end a transcription/termination signal and, if appropriate, further genetic control sequences which are linked operably to the interposed coding sequence of the fungal GTP cyclohydrolase II.

Also suitable are analogs of the above-described expression cassettes which can originate, for example, from a combination of the individual nucleic acid sequences on one polynucleotide (multiple constructs), more than one polynucleotide in a cell (co-transformation), or by sequential transformation.

Advantageous control sequences for the expression cassettes or vectors according to the invention are present, for example, in promoters such as the cos, tac, trp, tet, lpp, lac, lacIq, T7, T5, T3, gal, trc, ara, SP6, l-PR or in the l-PL promoter, all of which can be used for expressing fungal GTP cyclohydrolase II in Gram-negative bacterial strains.

Further advantageous control sequences are present for example in the promoters amy and SPO2, both of which can be used for expressing fungal GTP cyclohydrolase II in Gram-positive bacterial strains, and in the yeast or fungal promoters AUG1-, ADC1 GPD-1-, PX6-, TEF-, CUP1-, PGK-, GAP1-, TPI, PHO5-, AOX1, GAL10/CYC-1, CYC1, OliC-, ADH-, TDH-, Kex2-, MFa-, rp28- or the NMT-promotor or combinations of the aforementioned promoters (Degryse et al., Yeast 1995 Jun. 15; 11(7):629-40; Romanos et al. Yeast 1992 June; 8(6):423-88; Benito et al. Eur. J. Plant Pathol. 104, 207-220 (1998); Cregg et al. Biotechnology (N Y) 1993 August; 11 (8):905-10; Luo X., Gene 1995 Sep. 22; 163(1):127-31; Nacken et al., Gene 1996 Oct. 10; 175(1-2): 253-60; Turgeon et al., Mol Cell Biol 1987 September; 7(9): 3297-305) all of which can be used for expressing fungal GTP cyclohydrolase II in yeast strains. Examples of suitable terminators are the NMT-, Gcy1-, TrpC-, AOX1-, nos-, the PGK- or the CYC1-terminator, preferably the nos-terminator (Degryse et al., Yeast 1995 Jun. 15; 11(7):629-40; Brunelli et al. Yeast 1993 Dec. 9(12): 1309-18; Frisch et al., Plant Mol. Biol. 27 (2), 405-409 (1995); Scorer et al., Biotechnology (N.Y.) 12 (2), 181-184 (1994), Genbank acc. number Z46232; Zhao et al. Genbank acc number: AF049064; Punt et al., (1987) Gene 56 (1), 117-124).

Control elements which may be mentioned as being suitable for expression in insect cells are, for example, the polyhedrin promoter and the p10 promoter (Luckow, V. A. and Summers, M. D. (1988) Bio/Techn. 6, 47-55).

Examples of advantageous control sequences for expressing fungal GTP cyclohydrolase II in cell culture are, besides polyadenylation sequences, the following eukaryotic promoters of viral origin, such as, for example, promoters of the polyoma virus, adenovirus 2, cytomegalovirus or simian virus 40.

Further prokaryotic and eukaryotic expression systems are mentioned in Chapters 16 and 17 in Sambrook et al., Molecular Cloning: A Laboratory Manual. 2nd ed., Cold Spring Harbor Laboratory, Cold Spring Harbor Laboratory Press, Cold Spring Harbor, N.Y., 1989.

The expression cassettes according to the invention and the vectors derived from them may also comprise further functional elements, in addition to the abovementioned promoters. The following may be mentioned by way of example, but not by limitation: reporter genes, origins of replication, selection markers and/or affinity tags, fused to fungal GTP cyclohydrolase II either directly or by means of a linker optionally comprising a protease cleavage site.

The expression cassette and the vectors derived from them can be employed for the transformation of bacteria, cyanobacteria, yeasts, filamentous fungi and algae and eukaryotic cells (for example insect cells) with the purpose of recombinantly producing fungal GTP cyclohydrolase II, the generation of a suitable expression cassette depending on the organism in which the gene is to be expressed.

The nucleic acid encoding a fungal GTP cyclohydrolase II may advantageously also be introduced into the organisms in the form of a linear DNA and integrated into the genome of the host organism via heterologous or homologous recombination. This linear DNA may consist of a linearized plasmid or else only of the nucleic acid construct as vector or the nucleic acid sequences used. In a further advantageous embodiment, the nucleic acid sequences used in the method according to the invention may also be introduced into an organism by themselves. If, besides the nucleic acid sequences, further genes are to be introduced into the organism, all the genes may be introduced together into the organism in a single vector or each individual gene may be introduced into the organism in one vector each, it being possible to introduce the various vectors simultaneously or in succession.

The transgenic organisms generated by transformation can be used for recombinant expression of fungal GTP cyclohydrolase II.

Other preferred microorganisms for the recombinant expression are, besides bacteria, yeasts and fungi, and eukaryotic cell lines.

Preferred within the bacteria are bacteria of the genus *Escherichia*, *Erwinia*, *Flavobacterium*, *Alcaligenes* or cyanobacteria, for example of the genus *Synechocystis* or *Anabena*.

Preferred yeasts are *Candida*, *Saccharomyces*, *Hansenula* or *Pichia*.

Preferred fungi are *Aspergillus*, *Trichoderma*, *Ashbya*, *Neurospora*, *Fusarium*, *Beauveria*, *Mortierella*, *Saprolegnia*, *Pythium*, or other fungi described in Indian Chem. Engr. Section B. Vol 37, No 1, 2 (1995).

In principle, transgenic animals are also suitable as host organisms, for example *C. elegans*.

As aforementioned, also preferred is the use of expression systems and vectors which are publicly accessible or commercially available.

The typical advantageous commercially available fusion and expression vectors may be mentioned in this context: pGEX [Pharmacia Biotech Inc; Smith, D. B. and Johnson, K. S. (1988) Gene 67:31-40], pMAL (New England Biolabs, Beverly, Mass.) and pRIT5 (Pharmacia, Piscataway, N.J.) which comprises glutathion S-transferase (GST), Maltose binding protein, or protein A, the pTrc vectors (Amann et al., (1988) Gene 69:301-315), the "pKK233-2" from CLONTECH, Palo Alto, Calif. and the "pET" and "pBAD" vector series from Stratagene, La Jolla.

Further advantageous vectors for use in yeast are pYepSec1 (Baldari, et al., (1987) Embo J. 6:229-234), pMFa (Kurjan and Herskowitz, (1982) Cell 30:933-943), pJRY88 (Schultz et al., (1987) Gene 54:113-123), and pYES derivatives, pGAPZ derivatives, pPICZ derivatives, and the vectors of the "*Pichia* expression kit" (Invitrogen Corporation, San Diego, Calif.). Vectors for use in filamentous fungi are described in: van den Hondel, C.A.M.J.J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge.

As an alternative, insect cell expression vectors may also be used advantageously, for example for expression in Sf 9 cells. These are for example the vectors of the pAc series (Smith et al. (1983) Mol. Cell. Biol. 3:2156-2165) and the pVL series (Lucklow and Summers (1989) Virology 170:31-39). Others which may be mentioned are the baculovirus expression systems "MaxBac 2.0 kit" from Invitrogen, Carlsbad, or "BacPAK baculovirus expression system" from CLONTECH, Palo Alto, Calif.

Moreover, the fungal GTP cyclohydrolase II can be expressed in mammalian cells. Examples of such expression vectors are pCDM8 and pMT2P, which are mentioned in: Seed, B. (1987) Nature 329:840 or Kaufman et al. (1987) EMBO J. 6:187-195). In this complex, promoters to be used by preference are of viral origin such as, for example, promoters of polyoma virus, adenovirus 2, cytomegalovirus or simian virus 40. Further prokaryotic and eukaryotic expression systems are mentioned in Chapters 16 and 17 in Sambrook et al., Molecular Cloning: A Laboratory Manual. 2nd ed., Cold Spring Harbor Laboratory, Cold Spring Harbor Laboratory Press, Cold Spring Harbor, N.Y., 1989.

All above-mentioned organisms transformed with at least one of the above-mentioned expression cassettes or vectors are herein below termed as "transgenic organism according to the invention".

The fungal GTP cyclohydrolase II can be isolated from an organism naturally comprising a fungal GTP cyclohydrolase II, for example from the pathogenic fungi mentioned above and for example from fungi selected from the group consisting of the genera and species, e.g. *Pichia* such as *Pichia pastoris* and *Pichia methanolica*, *Saccharomyces* such as *Saccharomyces cerevisiae*, *Hansenula* such as *Hansenula poymorpha*; *Trichoderma*, *Ashbya* such as *Ashbya gossipii*, *Neurospora* such as *Neurospora crassa*, *Beauveria*, *Mortierella*, *Saprolegnia*, *Pythium*, or other fungi described in Indian Chem Engr. Section B. Vol 37, No 1, 2 (1995).

The selection according to step iv) is based on an in vivo assay. In a preferred embodiment this comprises the following steps:

a) the generation of a transgenic organism according to the invention which, following transformation with a nucleic acid sequence encoding a fungal GTP cyclohydrolase II, is capable of overexpressing polypeptide with GTP cyclohydrolase II activity;

b) the application, to the fungi of step a) and to an analogous, untransformed fungi, of a candidate compound;

c) the determination of the growth, the viability or infectivity of the transgenic and the untransformed organism following application of the substance of step b); and d) the selection of candidate compounds, which reduces growth, viability or infectivity of the transgenic and the untrans-formed fungi following application of the substance of step b).

In this step (c), compounds are selected which brought about a reduction in growth, viability or infectivity of at least 10%, advantageously at least 20%, preferably at least 30%, especially preferably by at least 50% and very especially preferably by at least 70%, or a 100% reduction (blocking) being achieved.

An analogous untransformed organism is to be understood as the fungi which has been used for generating the transgenic organism according to the invention in step a).

Suitable organisms are the fungi defined above, preferably those, which can be easily genetically manipulated by the skilled artisan, e.g. *Saccharomyces* species, *Pichia* species, *Fusarium* species, *Ashbya* species, *Schizosaccharomyces* species, *Magnaporte* species, *Ustilago* species, *Neurospora* species and *Klyveromyces* species.

When a sample comprising an antifungal agent has been identified by the method according to the invention, it is either possible to isolate the substance directly from the original samples, or else the sample can be divided into different groups, for example when it consists of a multiplicity of different components, in order to reduce the number of different substances per sample and then to repeat the method according to the invention with such a "subsample" of the original sample. Depending on the complexity of the sample, the above-described steps can be repeated several times, preferably until the sample identified in accordance with the method according to the invention only encompasses a small number of substances or only one substance. The substance identified in accordance with the method according to the invention, or derivatives thereof, is preferably formulated further so that it is suitable for use in plant breeding or in plant cell or plant tissue culture.

All of the antifungal agents identified by the above-mentioned methods can subsequently be tested for their fungicidal action in a further in-vivo activity test. Here, the substance in question is incubated with a culture of a pathogenic fungus, preferably a culture of a phytopathogenic fungus, especially preferably a culture of a filamentous phytopathogenic fungus, it being possible to determine the fungicidal action for example on the basis of limited growth.

The above-mentioned embodiments of the method for identifying antifungal agents are preferably realized in a high throughput screening. Using high throughput screening, many discrete compounds can be tested in parallel so that large numbers of candidate compounds can be quickly screened.

The most widely established techniques utilize 96-well, 384-well and 1536-well microtiter plates. The wells of the microtiter plates typically require assay volumes that range from 50 to 500 µl, preferably 200 µl. In addition to the plates, many instruments, materials, pipettors, robotics, plate washers, and plate readers are commercially available to fit the respective well format.

Alternatively, free format assays or assays that have no physical barrier between samples, can be used as described in Jayaickreme et al. (Proc. Natl. Acad. Sci. U.S.A. 19 (1994) 161418), Chelsky ("Strategies for Screening Combinatorial Libaries", First Annual Conference of The Society for Biomolecular Screening in Philadelphia, Pa. (Nov. 710, 1995)) and Salmon et al. (Molecular Diversity 2 (1996), 5763). Additionally, a high throughput screening method as described in U.S. Pat. No. 5,976,813 can be used based on a porous matrix, in which test samples are placed; one or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

It may be desirable for HTS to immobilize either the fungal GTP cyclohydrolase II or the candidate compound to facilitate separation of bound and unbound forms of one or both of the interactants, as well as to accommodate automation of the assay. Thus, either the fungal GTP cyclohydrolase II or the candidate compound is preferably bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the fungal GTP cyclohydrolase II or candidate compound to a solid support, including the use of covalent and non-covalent linkages, passive absorption, or pairs of binding moieties attached respectively to the fungal GTP cyclohydrolase II or candidate compound and the solid support. Candidate compounds are preferably bound to the solid support in an array, so that the location of individual candidate compounds can be tracked.

Binding of a candidate compound to a fungal GTP cyclohydrolase II can be accomplished in any vessel suitable for containing the reactants. Examples of such vessels include microtiter plates, test tubes, and microcentrifuge tubes.

All of the antifungal agents identified by the above-mentioned methods further designated as "identified compounds" are subject matter of the present invention. Preferably, they have a molecular weight below 1000 g/mol, preferably 500 g/mol, more preferably 400 g/mol and most preferably 300 g/mol. The identified compounds further exhibit a Ki value below 1 mM, preferably 1 µM, more preferably 0.1 µM and most preferably 0.01 µM.

The identified compounds may be: expression libraries, for example cDNA expression libraries, peptides, proteins, nucleic acids, antibodies, small organic substances, hormones, PNA(s) or the like (Milner, Nature Medicine 1 (1995), 879-880; Hupp, Cell. 83 (1995), 237-245; Gibbs, Cell. 79 (1994), 193-198 and references cited therein). They may be chemically synthesized substances or substances produced by microorganisms and can be present for example in cell extracts or, for example, plants, animals or microorganisms. The reaction mixture can be a cell-free extract or comprise a cell or cell culture. Suitable methods are known to the skilled worker and are described generally for example in Alberts, Molecular Biology the cell, $3^{rd}$ Edition (1994), for example Chapter 17. For example, the substances mentioned can be added to the reaction mixture or the culture medium or injected into the cells or sprayed onto a plant.

The identified compounds may also be present in the form of their agriculturally useful salts. Suitable salts among agriculturally useful salts are mainly the salts of those cations or the acid addition salts of those acids whose cations, or anions, respectively, do not adversely affect the fungicidal action of the identified compound.

All of the identified compounds—if they comprise asymmetrically substituted α-carbon atoms—exist either as racemates, enantiomer mixtures or as pure enantiomers and—if they have chiral substituents—may also exist as diastereomer mixtures. They are suitable for controlling the pathogenic fungi mentioned at the outset.

The invention therefore furthermore relates to processes for the preparation of the fungicidal composition, which comprises
a) selection of an identified compound; and
b) formulating the identified compound, or an agriculturally useful salt of the identified compound identified via (a), with suitable adjuvants.

The identified compounds according to the invention in step a) can be formulated for example in the form of directly sprayable aqueous solutions, powders, suspensions, also highly concentrated aqueous, oily or other suspensions or suspoemulsions or dispersions, emulsions, oil dispersions, pastes, dusts, compositions for spreading, or granules, and applied by spraying, atomizing, dusting, spreading or pouring. The use forms depend on the intended purposes and the nature of the identified compound used; in any case, they should ensure the finest possible distribution of the identified compounds according to the invention.

For the preparation of emulsions, pastes or aqueous or oil-containing dispersions, the identified compounds as such can be dissolved or dispersed in an oil or solvent, it being possible to add further formulation auxiliaries for homogenization. However, it is also possible to prepare liquid or solid concentrates which are composed of identified compound and, if appropriate, solvent or oil and optionally further auxiliaries, and these concentrates are suitable for dilution with water. Materials which may be mentioned in this context are emulsion concentrates (EC, EW), suspensions (SC), soluble concentrates (SL), pastes, pellets, wettable powders or granules, it being possible for the solid formulations to be either soluble or dispersible (wettable) in water. Moreover, such powders or granules or tablets may additionally be provided with a solid coating which prevents abrasion or an unduly early release of the identified compound.

The term auxiliaries is understood as meaning, in principle, the following classes of substances: antifoams, thickeners, wetters, stickers, dispersants or emulsifiers, bactericides and thixotropic agents. The skilled worked is familiar with the meaning of the abovementioned agents.

SLs, EWs and ECs can be prepared by simply mixing the constituents in question; powders can be prepared via mixing or grinding in specific types of mills (for example hammer mills). SCs and SEs are usually prepared by wet milling, it being possible to prepare an SE from an SC by adding an organic phase comprising further auxiliaries or identified compounds. The preparation is known. Granules, for example coating granules, impregnated granules and homogeneous granules, can be prepared by binding the identified compounds to solid carriers. The skilled worker is familiar with a multiplicity of solid carriers which are suitable for granules according to the invention, for example mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nutshell meal, cellulose powders or other solid carriers. The skilled worker is familiar with details of the preparation; they are stated, for example, in the following publications: U.S. Pat. No. 3,060,084, EP-A 707445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and ff. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989, and Mollet, H., Grubemann, A., Formulation technology, Wiley VCH Verlag GmbH, Weinheim (Federal Republic of Germany), 2001.

The skilled worker is familiar with a multiplicity of inert liquid and/or solid carriers which are suitable for the formulations according to the invention, such as, for example, liquid additives such as mineral oil fractions of medium to high boiling point, such as kerosene or diesel oil, furthermore coal tar oils and oils of vegetable or animal origin, aliphatic, cyclic and aromatic hydrocarbons, for example paraffin, tetrahydronaphthalene, alkylated naphthalenes or their derivatives, alkylated benzenes or their derivatives, alcohols such as methanol, ethanol, propanol, butanol, cyclohexanol, ketones such as cyclohexanone, or strongly polar solvents, for example amines such as N-methylpyrrolidone, or water.

The skilled worker is familiar with a multiplicity of surface-active substances (surfactants) which are suitable for the formulations according to the invention, such as, for example, the alkali, alkaline earth or ammonium salts of aromatic sulfonic acids, for example lignin sulfonic acid, phenol sulfonic acid, naphthalene sulfonic acid and dibutylnaphthalene-sulfonic acid, and of fatty acids, alkyl sulfonates, alkylaryl sulfonates, alkyl sulfates, lauryl ether sulfates and fatty alcohol sulfates, and salts of sulfated hexadecanols, heptadecanols and octadecanols, and of fatty alcohol glycol ethers; condensates of sulfonated naphthalene and its derivatives with formaldehyde, condensates of naphthalene or of the naphthalene sulfonic acids with phenol and formaldehyde, polyoxyethylene octylphenol ether, ethoxylated isooctylphenol, octylphenol or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylenealkyl ethers, lauryl alcohol polyglycol ether acetate, sorbitol esters, lignin-sulfite waste liquors or methylcellulose.

Powders, dusts and materials for spreading, being solid carriers, can be prepared advantageously by mixing or concomitantly grinding the active substances with a solid carrier.

The concentrations of the identified compounds in the ready-to-use preparations can be varied within wide limits and depend on the nature of the formulation in question.

The fungicidal compositions, or the identified compounds, can be applied in curative.

The applications of identified compounds (=substances and/or compositions) amount to from 0.001 to 3.0, preferably 0.01 to 1.0 kg/ha active substance, depending on the aim of the control measures, the season, the target plants and the stage of growth.

The present invention furthermore relates to a method of controlling harmful fungi, which comprises treating the fungi or the materials, plants, soils or seeds to be protected from fungal infection, with an effective amount of an antifungal agent according to the invention or of a fungicidal composition according to the invention. Harmful fungi are understood as meaning the pathogenic fungi mentioned at the outset.

Another object of the present invention is the use of the identified compounds for preparation of drugs, preferably pharmaceutical compositions comprising at least an identified compound. The identified compounds according to the invention can be administered orally or parenterally (subcutaneously, intravenously, intramuscularly and intraperitoneally) in a conventional way. Administration may also take place with vapors or sprays through the nasopharyngeal space.

The dosage depends on the age, condition and weight of the patient and on the mode of administration. As a rule, the daily dose of active substance is about 0.5-50 mg/kg of bodyweight on oral administration and about 0.1-10 mg/kg of bodyweight on parenteral administration.

The identified compounds can be used in conventional solid or liquid pharmaceutical forms, e.g. as uncoated or (film-) coated tablets, capsules, powders, granules, suppositories, solutions, ointments, creams or sprays. These are produced in a conventional way. For this purpose, the active substances can be processed with conventional pharmaceutical excipients such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The administration forms obtained in this way normally contain from 0.1 to 90% by weight of active substance.

The invention is now illustrated by the examples which follow, but are not limited thereto.

The recombinant methods on which the exemplary embodiments which follow are based are now described briefly:

A: General Methods

Cloning methods such as, for example, restriction cleavages, DNA isolation, agarose gel electrophoresis, purification of DNA fragments, transfer of nucleic acids to nitrocellulose and nylon membranes, linking of DNA fragments, transformation of *E. coli* cells, bacterial cultures, sequence analysis of recombinant DNA and Southern and Western Blots were carried out as described by Sambrook et al., Cold Spring Harbor Laboratory Press (1989) and Ausubel, F. M. et al., Current Protocols in Molecular Biology, Greene Publishing Assoc. and Wiley-Interscience (1994); ISBN 0-87969-309-6.

The bacterial strains used hereinbelow (*E. coli* XL1-blue) were obtained from BRL Gibco or Invitrogen, Carlsberg, Calif. The *Ashbya gossypii* wild-type strain has the ATTC number ATTC 10895.

B: Sequence Analysis of Recombinant DNA

Recombinant DNA molecules were sequenced using an ABI laser fluorescence DNA sequencer following the method of Sanger (Sanger et al., Proc. Natl. Acad. Sci. USA, 74, 5463-5467 (1977)). Fragments resulting from a polymerase chain reaction were sequenced and verified in order to avoid polymerase errors in constructs to be expressed.

C: Materials Used

Unless otherwise specified in the text, all of the chemicals used were obtained in analytical grade quality from Fluka (Neu-Ulm), Merck (Darmstadt), Roth (Karlsruhe), Serva (Heidelberg) and Sigma (Deisenhofen). Solutions were prepared using pure pyrogen-free water, referred to in the following text as $H_2O$, from a Milli-Q water system purification unit (Millipore, Eschborn). Restriction enzymes, DNA-modifying enzymes and molecular-biological kits were obtained from AGS (Heidelberg), Amersham (Brunswick), Biometra (Göttingen), Roche (Mannheim), Genomed (Bad Oeynnhausen), New England Biolabs (Schwalbach/Taunus), Novagen (Madison, Wis., USA), Perkin-Elmer (Weiterstadt), Pharmacia (Freiburg), Qiagen (Hilden) and Stratagene (Heidelberg). Unless otherwise specified, they were used following the manufacturer's instructions.

All of the media and buffers used for the genetic engineering experiments were sterilized either by filter sterilization or by heating in the autoclave.

EXAMPLE 1

A) Preparation of the Knock-Out Plasmid

The KO plasmid pDeltarib1G418 was obtained from pJR765 (WO95/26406) by inserting the G418R expression cassette (Degryse et al., Yeast 1995, 11(7):629-40) into pJR765 so that the GTP cyclohydrolase II gene (rib 1) that is set forth in SEQ ID NO:3 is deleted from 220 bp upstream the ATG codon to 739 bp downstream the ATG codon. 6 mg plasmid DNA of pDeltarib1G418 were linearized with the restriction enzyme Asp 700 and purified by classical gel elution for subsequent transformation.

B) Transformation of *Asbya goosypii*

*A. goosypii* spores were cultured for 12 h in MA2 medium (peptone 10 g/l, yeast extract 1 g/l, myoinositol 0.3 g/l, pH7) at 28° C. and 250 rpm. The cells were pelleted by classical centrifugation and suspended with phosphate buffer 50 mM, DTT 25 mM and incubated at 28° C. with low agitation for 30 min. The cells were collected by centrifugation and suspended with 25 ml cold phosphate buffer 50 mM pH 7.5; 150 μl of the cell suspension were mixed with 6 μg pDeltarib1 G418 treated with Asp 700. The mixture was electroporated with a Gene Pulser II electroporator (Bio-Rad; parameters: 200 ohms; 1.5 Kv; 25 μF)

Immediately after the electric pulse, the cells were mixed with 1 ml MA2 medium and spread on fresh Petri dishes containing MA2-agar supplemented with 200 mg vitamin b2. The plates were incubated at 28° C. for 6 h. Then, a fine layer of Top-agar (1% LMP agarose) containing G418 antibiotic 50 mg/ml was loaded at the top of the plates. The incubation was further conducted at 28° C. for 5 days. Several colonies capable of growth on selective medium were isolated for subsequent characterization.

C) Characterization of the KO Mutants

The KO mutants were grown on Petri dishes containing MA2 agar, G418 50 mg/ml and vitamin b2 200 mg/ml and then replicated on the same medium in the absence of vitamin b2. In the latter case, the KO mutants were not able to grow at all. This convincingly demonstrates that GTP cyclohydrolase II is essential for the life of the fungi.

EXAMPLE 2

A) Enzyme Preparation

*Ashbya gossypii* cells may be obtained after 2 days from a culture in 3% (w/v) malt extract+0.3% (w/v) difco-soyton, pH 5.6 at 28° C. A cell-free extract can be obtained by mechanical breakage of the cells with a kitchen blender in 50 mM imidazole buffer pH 7 containing 1 mM EDTA-Na salt, 5 mM $MgSO_4$, 10 mM KCl, 5 mM dithiothreitol and 30% (v/v) glycerol and separation of unbroken cells and debris by centrifugation.

B) Activity Assay

The assay is performed in a suitable buffer e.g. Tris/HCl, pH 7.8 including 1 mM $Mg.Cl_2$, 1 mM DTT, 0.5 mM NAD, 2 units/ml formate dehydrogenase and 2.5 mM GTP Li salt. After the addition of the GTP cyclohydrolase comprising cell free extracts of step A), the reaction was monitored by measuring the absorption at 340 nm.

After dissolving the respective candidate compounds in a suitable solvent e.g. DMSO, an aliquot of the afore made solution is added to the reaction mixture. The enzyme activity of this sample is compared with the activity of a control comprising the pure solvent instead of the candidate compound. The resulting relative activity was calculated as percent inhibition in relation to the sample without the candidate compound.

Figure 1:
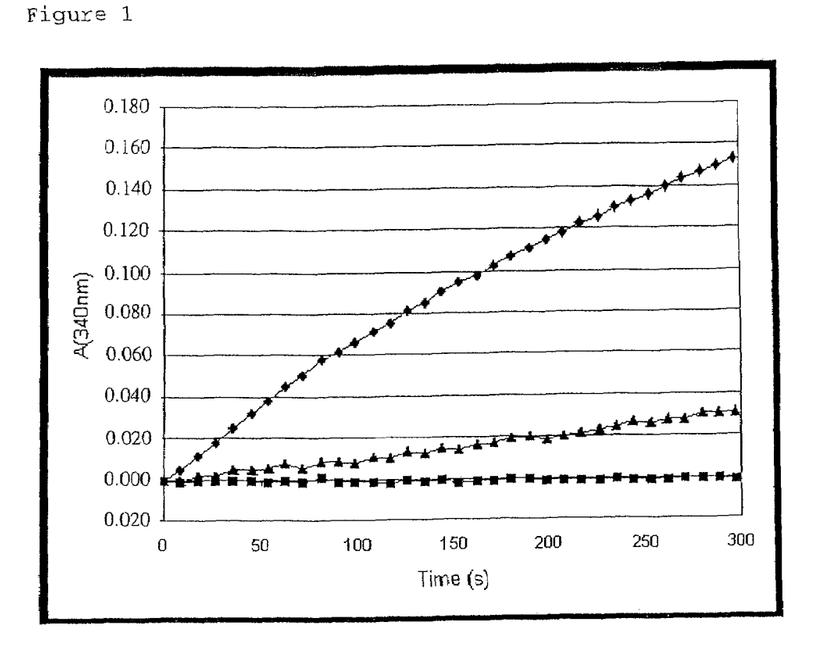
FIG. 1 shows the GTP dependent formation of NADH in the reaction mixture and inhibition by 3-butyl-10-(3-chlorophenyl)-10H-pyrimido[4,5-b]quinoline-2,4-dione. In this figure, ♦ designates values measured in the presence of GTP, ■ values measured without GTP and ▲ values measured in the presence of GTP and 3-butyl-10-(3-chlorophenyl)-10H-pyrimido[4,5-b]quinoline-2,4-dione.

In FIG. 1, the GTP dependant formation of NADH in the reaction mixture and inhibition by 3-Butyl-10-(3-chlorophenyl)-10H-pyrimido[4,5-b]quinoline-2,4-dione is shown.

Figure 2:
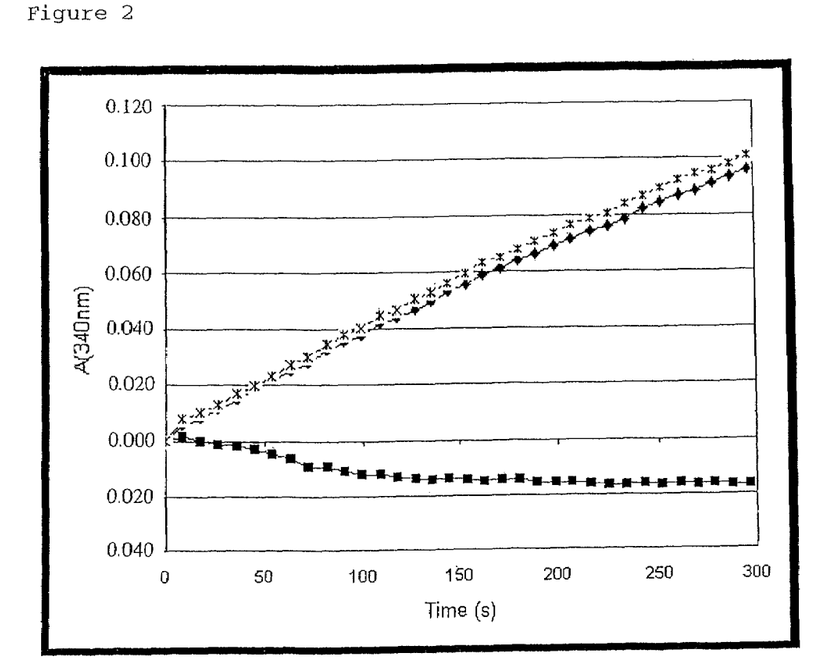
FIG. 2 shows the specificity of the inhibition by 3-butyl-10-(3-chlorophenyl)-10H-pyrimido[4,5-b]quinoline-2,4-dione. No inhibition of formate dehydrogenase alone is observed. Therefore, the inhibition of the GTP dependent NADH formation is a consequence of the inhibition of GTP cyclohydrolase. In this figure, ♦ designates values measured in the presence of formate, ■ values measured without formate and ★ values measured in the presence of formate and 3-butyl-10-(3-chlorophenyl)-10H-pyrimido[4,5-b]quinoline-2,4-dione.

To distinguish between the inhibition of GTP cyclohydrolase and formate dehydrogenase in the above-mentioned assay, the substrate GTP is replaced with formic acid. An inhibitor of GTP cyclohydrolase shows inhibition in the presence of GTP and no inhibition in the presence of formic acid (see e.g. FIG. 2).

c) Determination of fungicidal activity of 3-butyl-10-(3-chlorophenyl)-10H-pyrimido[4,5-b]quinoline-2,4-dione A stock solution of 3-butyl-10-(3-chlorophenyl)-10H-pyrimido[4,5-b]quinoline-2,4-dione is prepared in DMSO at a concentration of 10,000 ppm a.i. For the test, this is diluted with sterile deionized water to a concentration of 125 ppm; the DMSO concentration is constant at all test concentrations.

Spore suspensions of the fungi employed in the test (*Phytophthora infestans, Pyricularia oryzae* and *Septoria tritici*) are made in double strength growth medium (4% (w/v) malt extract in water).

For each fungal species, 3 (three) wells are prepared: 50 µl of compound solution are pipetted to each well, were to this are added 50 µl of spore suspension. A water/DMSO blank serves as the 100% growth control (=0 ppm); a well without added fungal inoculum but with the growth medium serves as medium blank.

The prepared plates are then incubated at 18° C. for 7 days after which the density of developed fungal mycelium is measured in a photometer at a wavelength of 405 nm.

After subtracting the medium blank readings and setting, the 100% growth control reading, the measurements from the concentration series are converted into "% growth compared with the 0 ppm control". The data set forth in table 1 clearly show that fungal growth was significantly inhibited by 3-butyl-10-(3-chlorophenyl)-10H-pyrimido[4,5-b]quinoline-2,4-dione.

TABLE 1

| *Pyricularia oryzae* *) | *Phytophthora infestans* *) | *Septoria tritici* *) |
|---|---|---|
| 47.6% | 39.9% | 0% |

*) [% growth compared with the 0 ppm control]

The invention claimed is:

1. A method for determination of GTP cyclohydrolase I or II activity comprising the steps of:
   a) adding GTP or GTP analog, NAD+ and formate dehydrogenase to a sample comprising GTP cyclohydrolase II or I;
   b) determining the production of NADH of the sample, and
   c) correlating the production of NADH with GTP I or II activity, wherein the production of NADH is indicative of GTP cyclohydrolase I or II activity.

2. The method of claim 1, wherein GTP is used as a substrate for the GTP cyclohydrolase and the production of NADH is determined by monitoring an increase in absorption at 340 nm.

3. The method of claim 1, wherein the determination of GTP cyclohydrolase I or II activity is by high-throughput screening.

* * * * *

SEQUENCE LISTING

```
<160> NUMBER OF SEQ ID NOS: 5

<210> SEQ ID NO 1
<211> LENGTH: 903
<212> TYPE: DNA
<213> ORGANISM: Ashbya gossipii
<220> FEATURE:
<221> NAME/KEY: CDS
<222> LOCATION: (1)..(903)

<400> SEQUENCE: 1 atg act gaa tac aca gtg cca gaa gtg acc tgt gtc gca cgc gcg cgc      48
Met Thr Glu Tyr Thr Val Pro Glu Val Thr Cys Val Ala Arg Ala Arg
  1               5                  10                  15 ata ccg acg gta cag ggc acc gat gtc ttc ctc cat cta tac cac aac      96
Ile Pro Thr Val Gln Gly Thr Asp Val Phe Leu His Leu Tyr His Asn
             20                  25                  30 tcg atc gac agc aag gaa cac cta gcg att gtc ttc ggc gag aac ata     144
Ser Ile Asp Ser Lys Glu His Leu Ala Ile Val Phe Gly Glu Asn Ile
         35                  40                  45 cgc tcg cgg agt ctg ttc cgg tac cgg aaa gac gac acg cag cag gcg     192
Arg Ser Arg Ser Leu Phe Arg Tyr Arg Lys Asp Asp Thr Gln Gln Ala
     50                  55                  60 cgg atg gtg cgg ggc gcc tac gtg ggc cag ctg tac ccc ggg cgg acc     240
Arg Met Val Arg Gly Ala Tyr Val Gly Gln Leu Tyr Pro Gly Arg Thr
 65                  70                  75                  80 gag gca gac gcg gat cgg cgt cag ggc ctg gag ctg cgg ttt gat gag     288
Glu Ala Asp Ala Asp Arg Arg Gln Gly Leu Glu Leu Arg Phe Asp Glu
                 85                  90                  95 aca ggg cag ctg gtg gtg gag cgg gcg acg acg tgg acc agg gag ccg     336
Thr Gly Gln Leu Val Val Glu Arg Ala Thr Thr Trp Thr Arg Glu Pro
            100                 105                 110 aca ctg gtg cgg ctg cac tcg gag tgt tac acg ggc gag acg gcg tgg     384
Thr Leu Val Arg Leu His Ser Glu Cys Tyr Thr Gly Glu Thr Ala Trp
        115                 120                 125 agc gcg cgg tgc gac tgc ggg gag cag ttc gac cag gcg ggt aag ctg     432
Ser Ala Arg Cys Asp Cys Gly Glu Gln Phe Asp Gln Ala Gly Lys Leu
    130                 135                 140 atg gct gcg gcg aca gag ggc gag gtg gtt ggc ggt gcg ggg cac ggc     480
Met Ala Ala Ala Thr Glu Gly Glu Val Val Gly Gly Ala Gly His Gly
145                 150                 155                 160 gtg atc gtg tac ctg cgg cag gag ggc cgc ggc atc ggg cta ggc gag     528
Val Ile Val Tyr Leu Arg Gln Glu Gly Arg Gly Ile Gly Leu Gly Glu
                165                 170                 175
```

```
aag ctg aag gcg tac aac ctg cag gac ctg ggc gcg gac acg gtg cag        576
Lys Leu Lys Ala Tyr Asn Leu Gln Asp Leu Gly Ala Asp Thr Val Gln
        180                 185                 190 gcg aac gag ctg ctc aac cac cct gcg gac gcg cgc gac ttc tcg ttg        624
Ala Asn Glu Leu Leu Asn His Pro Ala Asp Ala Arg Asp Phe Ser Leu
    195                 200                 205 ggg cgc gca atc cta ctg gac ctc ggt atc gag gac atc cgg ttg ctc        672
Gly Arg Ala Ile Leu Leu Asp Leu Gly Ile Glu Asp Ile Arg Leu Leu
210                 215                 220 acg aat aac ccc gac aag gtg cag cag gtg cac tgt ccg ccg gcg cta        720
Thr Asn Asn Pro Asp Lys Val Gln Gln Val His Cys Pro Pro Ala Leu
225                 230                 235                 240 cgc tgc atc gag cgg gtg ccc atg gtg ccg ctt tca tgg act cag ccc        768
Arg Cys Ile Glu Arg Val Pro Met Val Pro Leu Ser Trp Thr Gln Pro
                245                 250                 255 aca cag ggc gtg cgc tcg cgc gag ctg gac ggc tac ctg cgc gcc aag        816
Thr Gln Gly Val Arg Ser Arg Glu Leu Asp Gly Tyr Leu Arg Ala Lys
            260                 265                 270 gtc gag cgc atg ggg cac atg ctg cag cgg ccg ctg gtg ctg cac acg        864
Val Glu Arg Met Gly His Met Leu Gln Arg Pro Leu Val Leu His Thr
        275                 280                 285 tct gcg gcg gcc gag ctc ccc cgc gcc aac aca cac ata                    903
Ser Ala Ala Ala Glu Leu Pro Arg Ala Asn Thr His Ile
290                 295                 300

<210> SEQ ID NO 2
<211> LENGTH: 301
<212> TYPE: PRT
<213> ORGANISM: Ashbya gossipii

<400> SEQUENCE: 2

Met Thr Glu Tyr Thr Val Pro Glu Val Thr Cys Val Ala Arg Ala Arg
  1               5                  10                  15

Ile Pro Thr Val Gln Gly Thr Asp Val Phe Leu His Leu Tyr His Asn
                20                  25                  30

Ser Ile Asp Ser Lys Glu His Leu Ala Ile Val Phe Gly Glu Asn Ile
            35                  40                  45

Arg Ser Arg Ser Leu Phe Arg Tyr Arg Lys Asp Asp Thr Gln Gln Ala
        50                  55                  60

Arg Met Val Arg Gly Ala Tyr Val Gly Gln Leu Tyr Pro Gly Arg Thr
 65                  70                  75                  80

Glu Ala Asp Ala Asp Arg Arg Gln Gly Leu Glu Leu Arg Phe Asp Glu
                    85                  90                  95

Thr Gly Gln Leu Val Val Glu Arg Ala Thr Thr Trp Thr Arg Glu Pro
                100                 105                 110

Thr Leu Val Arg Leu His Ser Glu Cys Tyr Thr Gly Glu Thr Ala Trp
            115                 120                 125

Ser Ala Arg Cys Asp Cys Gly Glu Gln Phe Asp Gln Ala Gly Lys Leu
        130                 135                 140

Met Ala Ala Thr Glu Gly Glu Val Val Gly Gly Ala Gly His Gly
145                 150                 155                 160

Val Ile Val Tyr Leu Arg Gln Glu Gly Arg Gly Ile Gly Leu Gly Glu
                165                 170                 175

Lys Leu Lys Ala Tyr Asn Leu Gln Asp Leu Gly Ala Asp Thr Val Gln
                180                 185                 190

Ala Asn Glu Leu Leu Asn His Pro Ala Asp Ala Arg Asp Phe Ser Leu
            195                 200                 205
```

```
Gly Arg Ala Ile Leu Leu Asp Leu Gly Ile Glu Asp Ile Arg Leu Leu
    210                 215                 220
Thr Asn Asn Pro Asp Lys Val Gln Gln Val His Cys Pro Pro Ala Leu
225                 230                 235                 240
Arg Cys Ile Glu Arg Val Pro Met Val Pro Leu Ser Trp Thr Gln Pro
                245                 250                 255
Thr Gln Gly Val Arg Ser Arg Glu Leu Asp Gly Tyr Leu Arg Ala Lys
            260                 265                 270
Val Glu Arg Met Gly His Met Leu Gln Arg Pro Leu Val Leu His Thr
        275                 280                 285
Ser Ala Ala Ala Glu Leu Pro Arg Ala Asn Thr His Ile
    290                 295                 300

<210> SEQ ID NO 3
<211> LENGTH: 2528
<212> TYPE: DNA
<213> ORGANISM: Ashbya gossipii

<400> SEQUENCE: 3
atccgccgca aagggacgc catgctgctc acctccggcg agtcctcgcg ttgtcccgta      60
atgtccacat ccaccacgat cagctccgac gtcaccgtgt ggtccaccac cttgctcttg     120
acgctcacca gcgcctcgct cccgtcgctg gtaattatcc gcgcagaccc gtttgagtta     180
ggtaagaaat caaccgccac atccaagggg cggaactgcg ctgccgcccg cccgtctgcg     240
cgaatcggtg gtatcgcctt cagtgaatca atcagataca gctgctcggt cactgatagc     300
atcatggcta atttctgtcc gcatacttca tatgctcatc gcacattgat aatgtacatt     360
cgaaaaattt caagattagc ctccgtgaac agcgatttac cttaggcaaa agtaacaaaa     420
ggcttttccg taggtgcttt gtcattcaac aatccacgtc ggaattggcg actatatagt     480
gtagggccca taaagcagta gtcggtgttg atagctgtgt cagaccaact ctttgttaat     540
tactgaagct gatatgactg aatacacagt gccagaagtg acctgtgtcg cacgcgcgcg     600
cataccgacg gtacagggca ccgatgtctt cctccatcta taccacaact cgatcgacag     660
caaggaacac ctagcgattg tcttcggcga aacatacgc tcgcggagtc tgttccggta      720
ccggaaagac gacacgcagc aggcgcggat ggtgcgggc gcctacgtgg ccagctgta       780 cccgggcgg accgaggcag acgcggatcg gcgtcagggc ctggagctgc ggtttgatga      840
gacagggcag ctggtggtgg agcgggcgac gacgtggacc agggagccga cactggtgcg     900
gctgcactcg gagtgttaca cgggcgagac ggcgtggagc gcgcggtgcg actgcgggga     960
gcagttcgac caggcgggta agctgatggc tgcggcgaca gagggcgagg tggttggcgg    1020
tgcggggcac ggcgtgatcg tgtacctgcg gcaggagggc cgcggcatcg ggctaggcga    1080
gaagctgaag gcgtacaacc tgcaggacct gggcgcggac acggtgcagg cgaacgagct    1140
gctcaaccac cctgcggacg cgcgcgactt ctcgttgggg cgcgcaatcc tactggacct    1200
cggtatcgag gacatccggt tgctcacgaa taaccccgac aaggtgcagc aggtgcactg    1260
tccgccggcg ctacgctgca tcgagcgggt gcccatggtg ccgctttcat ggactcagcc    1320
cacacagggc gtgcgctcgc gcgagctgga cggctacctg cgcgccaagg tcgagcgcat    1380
ggggcacatg ctgcagcggc cgctggtgct gcacacgtct gcggcggccg agctccccg     1440 cgccaacaca cacatataat ctttgctata ttaaaactct ataaacgtat gccacacggc    1500
gcccgcgggc tgccacacgc tgctcacggg ctgccgaaca gttctaacaa gtaatcgcgc    1560
```

-continued

```
gcctcgccag tgatcgtggc gagcaccttg tcgtccatca tcacatatcc tcggctacag      1620
tcgtcgttga agagcgtcga cgtgcgcttc gacttgtgcg atttaaggaa gtcgttgtat      1680
ccgttgaccg tggttagctc gaccggcgcg ctaacgagaa acgatcctgt ggaacccgtg      1740
gactcggacg actggaattg cgattggttc ttaagcttgt atagggtctg catcttctgt      1800
gttcagcttg gggatcgcgg acggttttgt cacccacggt ctagtagtcg catttatata      1860
ctagcgtact agccgcccct agctggtccc gggaggggga gcgtcgccat cggttacggg      1920
tcacgtggtt ttggtcgaag gcaatcgaag cgtcagggga gattctatgt gatgtctggg      1980
tatttgtacg gctgacgcac gtgactggcg gcataagtgt cagcacgcca gacgtgacgc      2040
gagccgcacg agccgtgcgg cactgactgc tgcgattggc gcgcatctca accacggatg      2100
aggggtccgc ttatggtcat gagcttagta aacttctgat tatattaaag aatcatactc      2160 ataaacatt caacgatata tcattctatt taaccactca agaataaacc tctaagtata      2220
ttacagaggt catatacata ttagattata caacagatta gtgtatttct tatctcacgt      2280
ataaacaaat aagtagattg gaggattcat atcagatatt aatgtaagac tcatattaaa      2340
ttcttagttc cttacaagtt taaacttcta agtatattga agaggtcata cttgaattaa      2400
actatacgat agatgatact cttttctttc tcttcgatta tattaaatga ttagtatatt      2460
atatgccatt tgataaaatg attgatatat tacaatatta tctttaatat tttaataata      2520
acaaatat                                                              2528
```

<210> SEQ ID NO 4
<211> LENGTH: 582
<212> TYPE: DNA
<213> ORGANISM: Fusarium graminearum
<220> FEATURE:
<221> NAME/KEY: CDS
<222> LOCATION: (1)..(582)

<400> SEQUENCE: 4

```
act ctc ccg gag gtg gaa tgc atc gtt cgt gcc cgt atc ccc acg gtt        48
Thr Leu Pro Glu Val Glu Cys Ile Val Arg Ala Arg Ile Pro Thr Val
  1               5                  10                  15 gca gga acc gag atg ttc ttg cac ctg tac acc aac aat gtg gac aac        96
Ala Gly Thr Glu Met Phe Leu His Leu Tyr Thr Asn Asn Val Asp Asn
             20                  25                  30 aag gag cac ctc gcc atc gtg ttt ggc aaa aat atc cga agc aag agt       144
Lys Glu His Leu Ala Ile Val Phe Gly Lys Asn Ile Arg Ser Lys Ser
         35                  40                  45 cta gat gct gtc cgg gag ggt gag acc gag atg gac cgc atg gtg cgc       192
Leu Asp Ala Val Arg Glu Gly Glu Thr Glu Met Asp Arg Met Val Arg
     50                  55                  60 ggc gca tac aca gga agg ctg ttc ccc ggt cgc aca acc agt ggc atc       240
Gly Ala Tyr Thr Gly Arg Leu Phe Pro Gly Arg Thr Thr Ser Gly Ile
 65                  70                  75                  80 ggt cca gcg acc cct cag gag gaa cag cca ccg cag ccg tcg gat gag       288
Gly Pro Ala Thr Pro Gln Glu Glu Gln Pro Pro Gln Pro Ser Asp Glu
                 85                  90                  95 cct cct ctg gtg agg att cat tcc gag tgc tac aca ggt gag acg gcg       336
Pro Pro Leu Val Arg Ile His Ser Glu Cys Tyr Thr Gly Glu Thr Ala
            100                 105                 110 tgg tca gcg cga tgc gac tgc ggc gag cag ctc gat gaa gca gcg cgc       384
Trp Ser Ala Arg Cys Asp Cys Gly Glu Gln Leu Asp Glu Ala Ala Arg
        115                 120                 125 ctg atg agt ctg cca ggc aac aag gcc ggc ggc atc atc atc tac ctg       432
Leu Met Ser Leu Pro Gly Asn Lys Ala Gly Gly Ile Ile Ile Tyr Leu
```

-continued

```
                    130                 135                 140
cga caa gag ggt cgt ggt atc ggt ctg gga gag aag ctc aag gcg tac       480
Arg Gln Glu Gly Arg Gly Ile Gly Leu Gly Glu Lys Leu Lys Ala Tyr
145                 150                 155                 160 aat ctt cag gat ctg ggg tct gat act gtc gag gcg aat ttg ctt ttg       528
Asn Leu Gln Asp Leu Gly Ser Asp Thr Val Glu Ala Asn Leu Leu Leu
                    165                 170                 175 cgc cat cct gcc gat gct cga agc tac ggt ctt gct acc gct atg ctg       576
Arg His Pro Ala Asp Ala Arg Ser Tyr Gly Leu Ala Thr Ala Met Leu
                180                 185                 190 ctg gat                                                               582
Leu Asp <210> SEQ ID NO 5
<211> LENGTH: 194
<212> TYPE: PRT
<213> ORGANISM: Fusarium graminearum

<400> SEQUENCE: 5

Thr Leu Pro Glu Val Glu Cys Ile Val Arg Ala Arg Ile Pro Thr Val
 1               5                  10                  15

Ala Gly Thr Glu Met Phe Leu His Leu Tyr Thr Asn Val Asp Asn
                20                  25                  30

Lys Glu His Leu Ala Ile Val Phe Gly Lys Asn Ile Arg Ser Lys Ser
            35                  40                  45

Leu Asp Ala Val Arg Glu Gly Glu Thr Glu Met Asp Arg Met Val Arg
        50                  55                  60

Gly Ala Tyr Thr Gly Arg Leu Phe Pro Gly Arg Thr Thr Ser Gly Ile
65                  70                  75                  80

Gly Pro Ala Thr Pro Gln Glu Glu Gln Pro Gln Pro Ser Asp Glu
                85                  90                  95

Pro Pro Leu Val Arg Ile His Ser Glu Cys Tyr Thr Gly Glu Thr Ala
            100                 105                 110

Trp Ser Ala Arg Cys Asp Cys Gly Glu Gln Leu Asp Glu Ala Ala Arg
        115                 120                 125

Leu Met Ser Leu Pro Gly Asn Lys Ala Gly Gly Ile Ile Ile Tyr Leu
    130                 135                 140

Arg Gln Glu Gly Arg Gly Ile Gly Leu Gly Glu Lys Leu Lys Ala Tyr
145                 150                 155                 160

Asn Leu Gln Asp Leu Gly Ser Asp Thr Val Glu Ala Asn Leu Leu Leu
                165                 170                 175

Arg His Pro Ala Asp Ala Arg Ser Tyr Gly Leu Ala Thr Ala Met Leu
            180                 185                 190

Leu Asp
```